(12) United States Patent
Xu et al.

(10) Patent No.: US 12,318,537 B2
(45) Date of Patent: Jun. 3, 2025

(54) RESPIRATORY APPARATUS WITH NOISE-DAMPING MEMBER

(71) Applicants: VINCENT MEDICAL (DONG GUAN) MANUFACTURING CO., LTD., Guangdong (CN); VINCENT MEDICAL (DONGGUAN) TECHNOLOGY CO., LTD., Guangdong (CN)

(72) Inventors: Jiebing Xu, Guangdong (CN); Haibin Yu, Guangdong (CN); Zhenxiang Hu, Guangdong (CN); Yu Lei, Guangdong (CN)

(73) Assignees: VINCENT MEDICAL (DONG GUAN) MANUFACTURING CO., LTD., Guangdong (CN); VINCENT MEDICAL (DONGGUAN) TECHNOLOGY CO., LTD., Guangdong (CN)

( * ) Notice: Subject to any disclaimer, the term of this patent is extended or adjusted under 35 U.S.C. 154(b) by 885 days.

(21) Appl. No.: 17/437,215

(22) PCT Filed: Jun. 6, 2019

(86) PCT No.: PCT/CN2019/090389
§ 371 (c)(1),
(2) Date: Sep. 8, 2021

(87) PCT Pub. No.: WO2020/243958
PCT Pub. Date: Dec. 10, 2020

(65) Prior Publication Data
US 2022/0168522 A1 Jun. 2, 2022

(51) Int. Cl.
*A61M 16/00* (2006.01)
*A61M 16/10* (2006.01)
(Continued)

(52) U.S. Cl.
CPC .... *A61M 16/0066* (2013.01); *A61M 16/1005* (2014.02); *A61M 16/105* (2013.01);
(Continued)

(58) Field of Classification Search
CPC .................................................. A61M 2205/42
See application file for complete search history.

(56) References Cited

U.S. PATENT DOCUMENTS

| 6,279,574 B1 | 8/2001 | Richardson et al. |
| 7,497,215 B1 * | 3/2009 | Nguyen ............ A61M 16/0057 |
| | | 128/205.27 |

(Continued)

FOREIGN PATENT DOCUMENTS

| CN | 100587804 C * | 2/2010 |
| CN | 202105279 U | 1/2012 |

(Continued)

OTHER PUBLICATIONS

Office Action dated May 5, 2023 issued by the Japanese Patent Office for corresponding Japanese Patent Application No. 2021-564103.
(Continued)

*Primary Examiner* — Joseph D. Boecker
*Assistant Examiner* — Thomas W Greig
(74) *Attorney, Agent, or Firm* — HOWSON & HOWSON LLP

(57) ABSTRACT

A respiratory apparatus, comprising: a first gas inlet for supplying a first gas to the respiratory apparatus; a second gas inlet connectable to a pressurized gas source to supply a pressurized gas; a mixing chamber for mixing the first gas and the pressurized gas; and a noise-damping member disposed downstream of the mixing chamber.

18 Claims, 10 Drawing Sheets

(51) Int. Cl.
*A61M 16/12* (2006.01)
*A61M 16/16* (2006.01)

(52) U.S. Cl.
CPC ............ *A61M 16/12* (2013.01); *A61M 16/16* (2013.01); *A61M 2205/3327* (2013.01); *A61M 2205/3334* (2013.01); *A61M 2205/42* (2013.01)

(56) References Cited

U.S. PATENT DOCUMENTS

| | | | |
|---|---|---|---|
| 2004/0231913 A1 | 11/2004 | McCombs et al. | |
| 2008/0127976 A1* | 6/2008 | Acker | A61M 16/08 128/204.18 |
| 2009/0007912 A1* | 1/2009 | Lindell | A61M 16/10 128/204.18 |
| 2009/0260629 A1* | 10/2009 | Yee | A61M 16/12 128/204.18 |
| 2012/0145155 A1 | 6/2012 | Peake et al. | |
| 2013/0263854 A1 | 10/2013 | Taylor et al. | |
| 2014/0299132 A1 | 10/2014 | Librett et al. | |
| 2015/0059745 A1 | 3/2015 | Barker et al. | |
| 2015/0120067 A1 | 4/2015 | Wing et al. | |
| 2016/0082220 A1* | 3/2016 | Barker | A61M 16/1005 128/203.12 |
| 2017/0281893 A1* | 10/2017 | Kwok | A61M 16/065 |
| 2019/0255276 A1* | 8/2019 | Van Schalkwyk | A61M 16/16 |
| 2019/0269874 A1* | 9/2019 | Barker | G01N 29/024 |
| 2020/0282172 A1* | 9/2020 | Mulfinger | A61M 16/125 |

FOREIGN PATENT DOCUMENTS

| | | |
|---|---|---|
| CN | 104548296 A | 4/2015 |
| CN | 105963838 A | 9/2016 |
| CN | 109675158 A | 4/2019 |
| CN | 208770599 U | 4/2019 |
| CN | 109718453 A | 5/2019 |
| EP | 2826510 A1 | 1/2015 |
| JP | S56-146096 A | 11/1981 |
| JP | H03-1867 A | 1/1991 |
| JP | 2001-278604 A | 10/2001 |
| JP | 2002-317464 A | 10/2002 |
| JP | 2013-071004 A | 4/2013 |
| JP | 2015-512320 A | 4/2015 |
| WO | 2014/145912 A1 | 9/2014 |
| WO | 2018/222561 A1 | 12/2018 |

OTHER PUBLICATIONS

European Search Report for corresponding EP Application No. 19931932.8, Feb. 6, 2023.
Office Action dated Dec. 8, 2022 issued by the Japanese Patent Office for corresponding Japanese Patent Application No. 2021-564103.
International Search Report and Written Opinion of the International Searching Authority issued for International PCT Application No. PCT/CN2019/090389 on Feb. 26, 2020.

* cited by examiner

RESPIRATORY APPARATUS WITH NOISE-DAMPING MEMBER

CROSS-REFERENCE TO RELATED APPLICATION(S)

This is a national stage application filed under 37 U.S.C. 371 based on International Patent Application No. PCT/CN2019/090389, filed Jun. 6, 2019, the disclosures of which is incorporated herein by reference in its entirety.

TECHNICAL FIELD

The present invention relates to a respiratory apparatus particularly a respiratory apparatus requiring a supply of a pressurized gas.

BACKGROUND OF THE INVENTION

In modern clinical medicine, a respiratory apparatus is commonly used for patients with respiratory illnesses such as acute respiratory distress syndrome, severe asthma and chronic obstructive pulmonary disease, as well as used for anesthesia and respiratory management during surgery, first aid resuscitation, and even domestic use for supportive treatment. A respiratory apparatus is a vital medical device that can prevent and treat respiratory failure, reduce complications and prolong the patient's life.

Current respiratory apparatuses possess a number of drawbacks. For example, when air is drawn into a respiratory apparatus by a blower, noise is generated by the friction between the air flow and the gas inlet passage. The noise is particularly obvious when the respiratory apparatus is used in a quiet environment or when the patient is sleeping, potentially causing a physical and mental annoyance to the patient. Further, it can be difficult to monitor the gas composition or gas flow rate when there are substantial high frequency noises. The high frequency noises may be generated when supplying a high pressure gas and these can affect the detection conducted by a sensor in the respiratory apparatus.

It is therefore desirable to provide an improved respiratory apparatus with a sensor working effectively to monitor the gas flow and gas content, and/or a respiratory apparatus with reduced noises.

SUMMARY OF THE INVENTION

The present invention provides a respiratory apparatus which can at least solve the technical problem of the noise generated by/at the gas inlet of the current respiratory apparatus, and/or improve the measurement of concentration of gas to be delivered to a user.

According to an aspect of the present invention, there is provided a respiratory apparatus including a first gas inlet for supplying a first gas to the respiratory apparatus; a second gas inlet connectable to a pressurized gas source to supply a pressurized gas; a mixing chamber for mixing the first gas and the pressurized gas, and a noise-damping member disposed downstream of the mixing chamber.

In an embodiment, the respiratory apparatus further comprises a noise reduction device mounted on the respiratory apparatus, wherein the noise reduction device is in fluid communication with the first gas inlet. The noise reduction device comprises a body having a side wall and a noise reduction device gas outlet, and a cover configured to be detachably engageable with the body for forming a noise-reduction device gas inlet and a gas passage.

Without intending to be limited by theory, it is believed that the respiratory apparatus of the present invention substantially minimize possible noises generated during supply of the pressurized gas and the supply of atmospheric air driven by a blower. The noise-damping member herein is particularly useful to improve the measurement conducted by one or more sensors arranged on, or in the respiratory apparatus, and especially those susceptible to frequency noises.

DETAILED DESCRIPTION OF THE INVENTION

Figure 1:
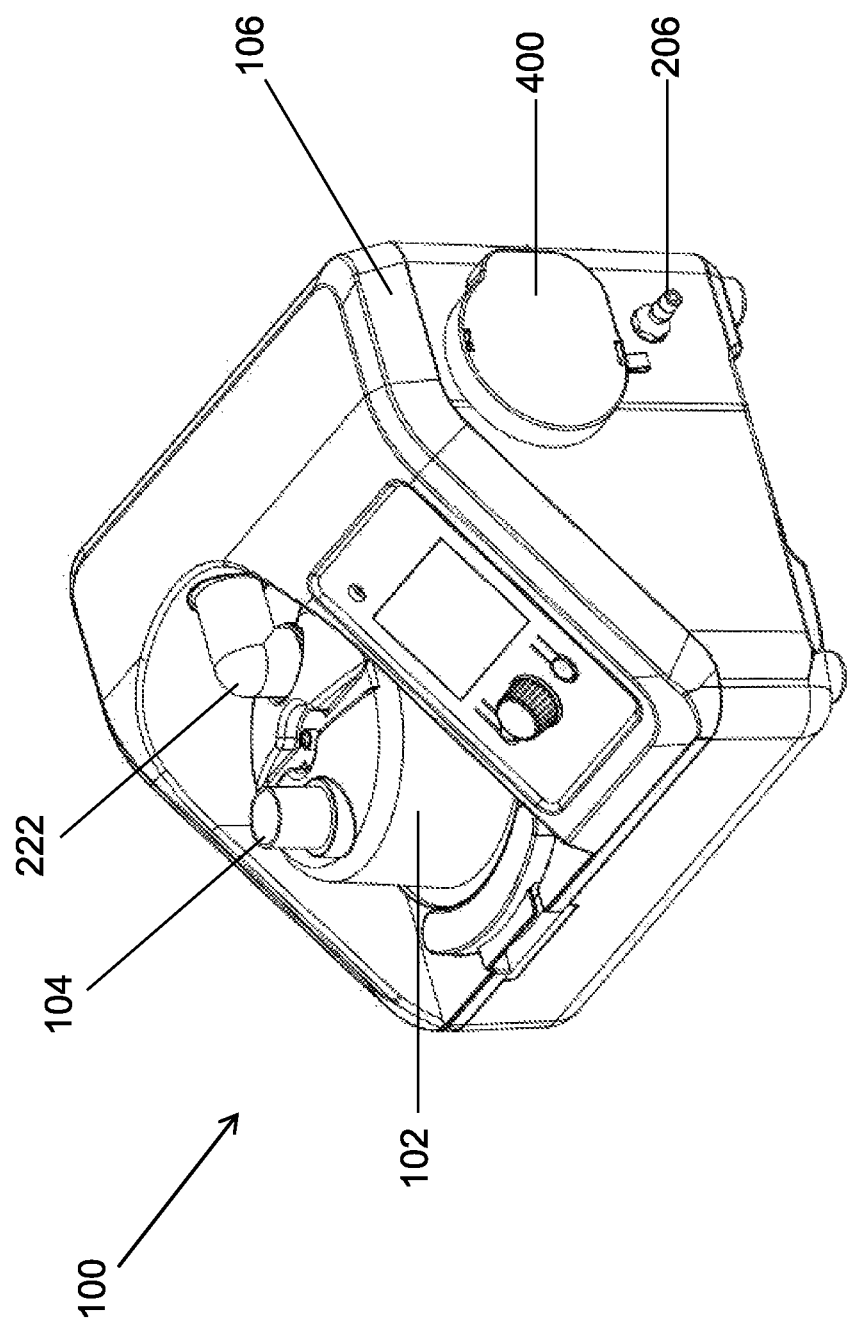
FIG. 1 shows an embodiment of the respiratory apparatus of the present invention.

The present invention relates to a respiratory apparatus which requires a supply of a pressurized gas. The respiratory apparatus may be, but is not limited to, a humidifier, a respirator, a nebulizer, a continuous positive air pressure machine, an automatic positive air pressure machine, etc.

In an embodiment of the present invention, the respiratory apparatus includes a first gas inlet for supplying a first gas to the respiratory apparatus; a second gas inlet connectable to a pressurized gas source to supply a pressurized gas; a mixing chamber for mixing the first gas and the pressurized gas, and a noise-damping member disposed downstream of the mixing chamber. The first gas inlet and the second inlet are separate from each other allowing two streams of gas to enter the respiratory independently. In this context, the pressurized gas entered via the second gas inlet is considered as a second gas.

The gas useful herein typically includes atmospheric air, air enriched with oxygen gas, etc., as desired. In an embodiment, the first gas is atmospheric air which may be supplied to the respiratory apparatus at ambient room temperature, higher than room temperature, or lower than room temperature, as desired. In an embodiment, the first gas is at the ambient pressure of the surrounding environment and at ambient room temperature. In an embodiment, the second gas or the pressurized gas is provided by a pressurized gas source which may be, but not limited to, a compressed oxygen gas tank. The pressurized gas may be oxygen which is at a higher pressure than the surrounding environment. Other suitable pressurized gas may also be used according to the desired operation.

In an embodiment, the mixing chamber is in fluid communication with the first and second gas inlet. The mixing chamber has two separate ports, a first port and a second port for respectively receiving the first gas and the second gas from the first and second gas inlet. The first port and the second port may be arranged on different surface of the mixing chamber so that when the two streams of gas enter into the mixing chamber, they may, for example, generate a vortex and mix with each other resulting in a mixed stream of gas. In a particular embodiment, the first port is arranged to be perpendicular to or at angle with respect to the second port so as to thoroughly mix the two streams of gas.

The mixing chamber of the present invention has a gas outlet for discharging the mixed stream of gas towards other parts of the respiratory apparatus for example a humidifying chamber, a drug adding chamber, a heating chamber or the like. In an embodiment, the mixed stream of gas is discharged towards a humidifying chamber for further processing before delivering to a user so that the delivered gas is at the optimum conditions.

However, it has been found that the mixing of a first gas and a second gas may cause enough noise and/or noise of a frequency (e.g., a whining or whistling noise) to bother users, especially when they are attempting to rest and/or sleep. It has further been found that this noise can be especially loud and/or annoying due to the frequency thereof. In addition, it has been found that the noise can be exacerbated when a gas is mixed with a pressurized gas.

Accordingly, the respiratory apparatus herein includes a noise-damping member disposed downstream of the mixing chamber for minimizing possible noises generated during supply of the pressurized gas. The noise-damping member is particularly useful to improve the measurement conducted by one or more sensors arranged on, or in the respiratory apparatus. It is particularly advantageous for the respiratory apparatus having an ultrasonic sensor which is susceptible to high frequency noises.

In an embodiment, the noise-damping member is in fluid communication with the mixing chamber, for example along the flow path of the mixed stream of gas discharging from the mixing chamber. The provision of the noise-damping member along the flow path effectively minimizes possible noises generated during operation. The noise-damping member is useful to absorb and/or reduce the noises generated in particular high frequency noises. In an embodiment, the noise-damping member is made of a sound absorbing material particularly, but not limited to, a sintered material. The sound absorbing material may be a porous material, for example, porous ceramic, porous plastics or porous polymeric foams, for absorbing noise. In an embodiment, the sound absorbing material is a sintered plastic, optionally porous, selected from sintered polyethylene (PE), sintered polyamide (PA), sintered polytetrafluoroethylene (PTFE), or sintered polyvinylidene fluoride (PVDF). In another embodiment, the noise-damping member is made of a metallic sintered material, optionally porous, and may include one or more of silver, nickel, titanium, aluminum, steel, stainless steel, bronze and the like.

The noise-damping member may be configured in any shape to be positioned along the flow path so as to absorb or reduce the undesirable noises. In an embodiment, the noise-damping member may be cylindrical, or in the form of a C-shape or a mesh. In another embodiment, the noise-damping member may be configured as a membrane or a filter which is permeable to gas, and such a noise-damping member may further act as a turbulence filter to minimize turbulence in the gas before discharging the gas to other part of the respiratory apparatus, thereby reducing noises. The respiratory apparatus may include more than one noise-damping member and each noise-damping member may be configured in different shape and provided at different position along the flow path, and preferably downstream of the mixing chamber.

Furthermore, it has been surprisingly found that the absorption and/or reduction of the undesirable noises helps to improve the accuracy of the measurements conducted by the sensor, especially an ultrasonic sensor; or a high frequency ultrasonic sensor.

In an embodiment, the respiratory apparatus has a sensor for determining the concentration of one or more gas components in the first gas, the pressurized gas or the mixed stream of gas. The sensor may be an ultrasonic sensor particularly a high frequency ultrasonic sensor. In an embodiment, an ultrasonic sensor is arranged downstream of the mixing chamber to determine the concentration of the mixed stream of gas, and/or before entering next processing chamber such as the humidifying chamber. In a particular embodiment, the ultrasonic sensor is disposed downstream of the noise-damping member so as to effectively minimize the noises generated.

In order to better monitor the air flow in the respiratory apparatus, the respiratory apparatus may further include a flow sensor for determining a flow rate of the gas in particular the mixed stream of gas towards the humidifying chamber. Flow sensors that are typically known in the art may be applied in the present invention anywhere within flow path.

The respiratory apparatus of the present invention may further include a noise reduction device and that the noise reduction device is in fluid communication with the first gas inlet. The combination with the noise reduction device can further help to reduce possible noises generated at the first gas inlet.

Turning to the figures, FIG. 1 shows an embodiment of a respiratory apparatus 100 which is provided as a humidifier to supply humidified gas to a user. The respiratory apparatus 100 has a gas mixing mechanism (see 200 at FIG. 2) therein for facilitating the supply of gas to a humidifying chamber 102 for processing. After processing, the humidified gas will be delivered to a user via a breathing circuit connected to a discharge port 104 on the humidifying chamber 102.

Figure 2:
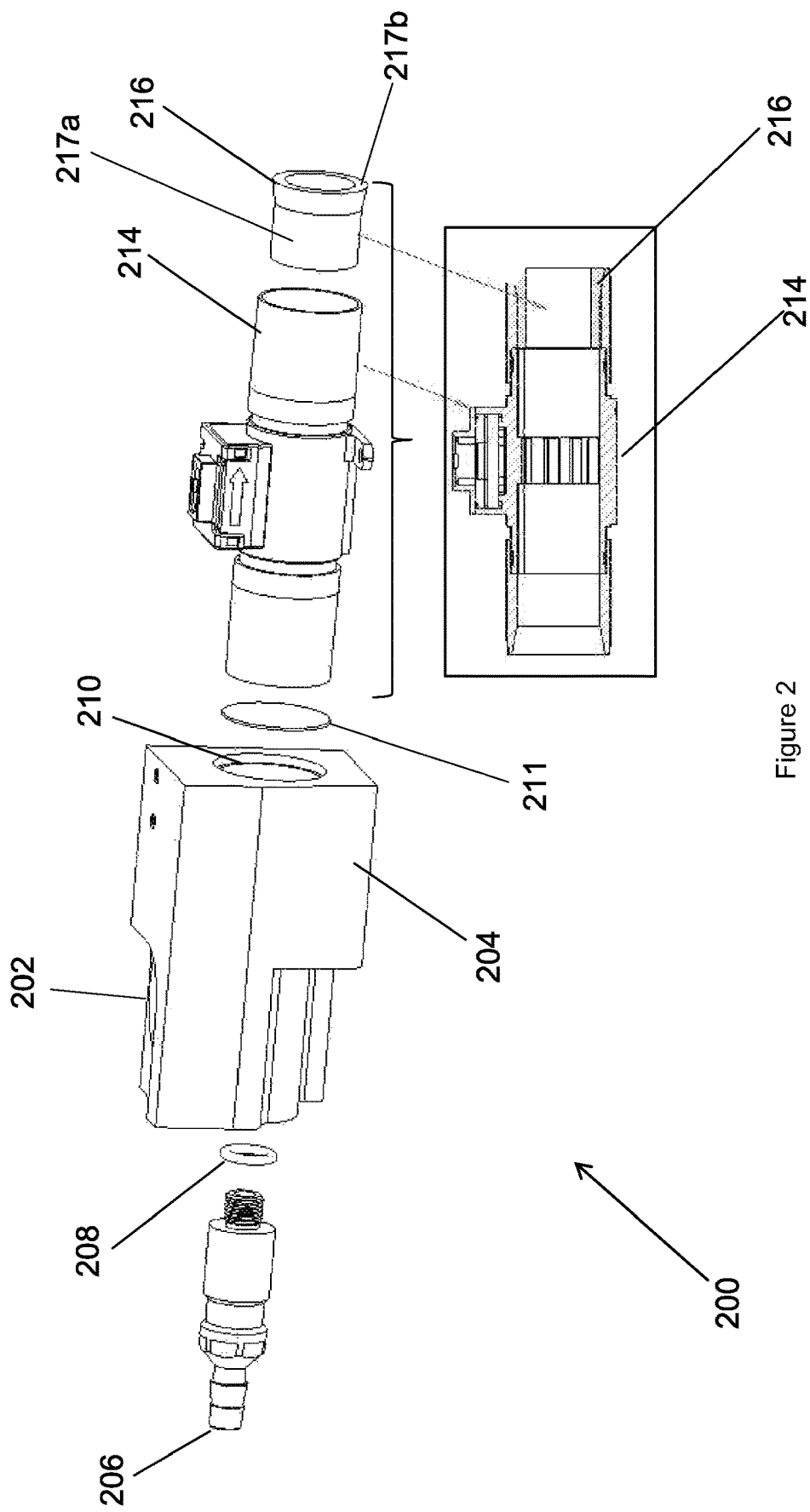
FIG. 2 shows a gas mixing mechanism in an embodiment of the respiratory apparatus, as well as a cross-sectional view of the installation of a noise-damping member in a flow sensor.
Figure 3A:
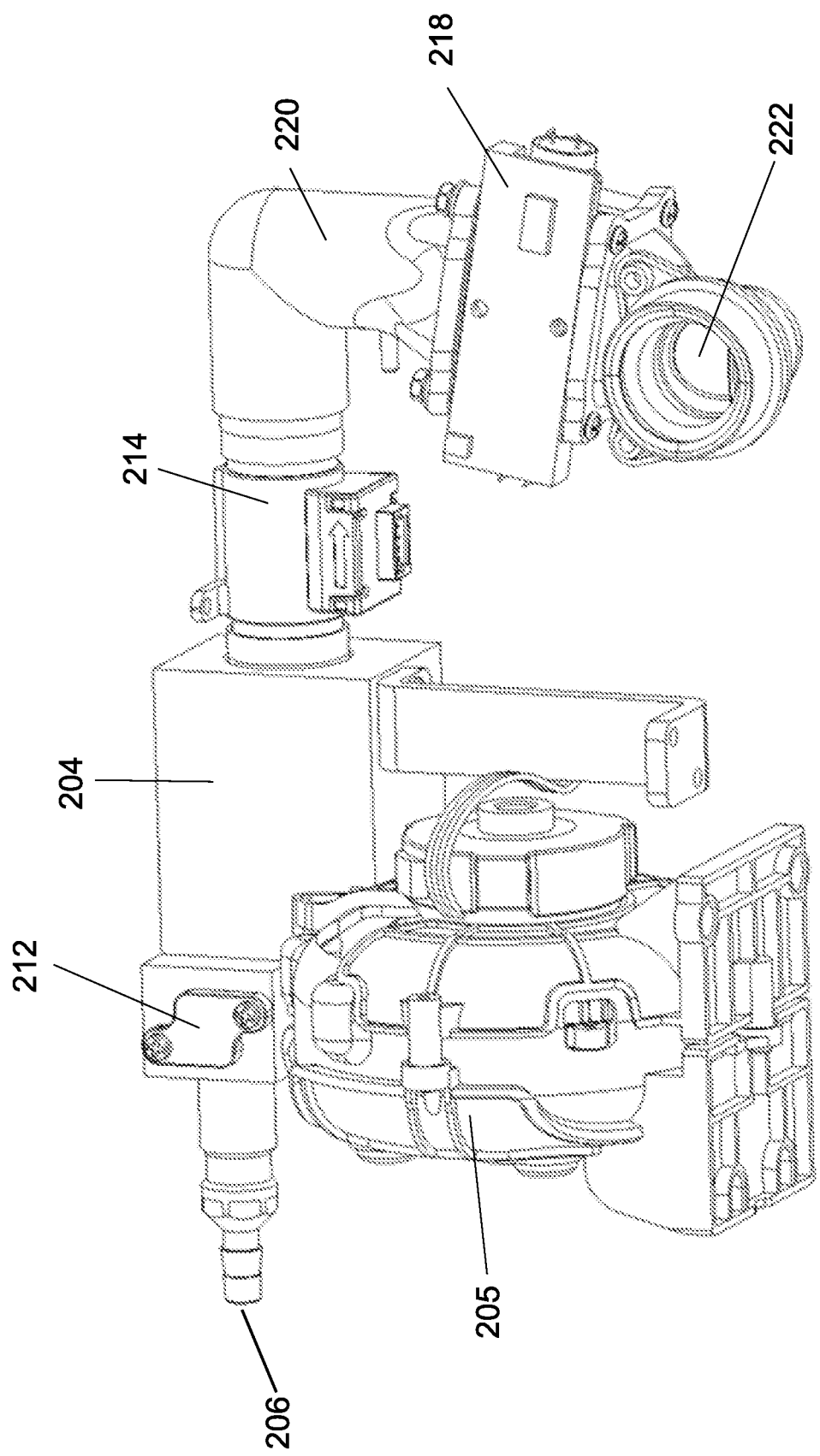
FIG. 3a shows the arrangement of the gas mixing mechanism together with the blower and an ultrasonic sensor.
Figure 3B:
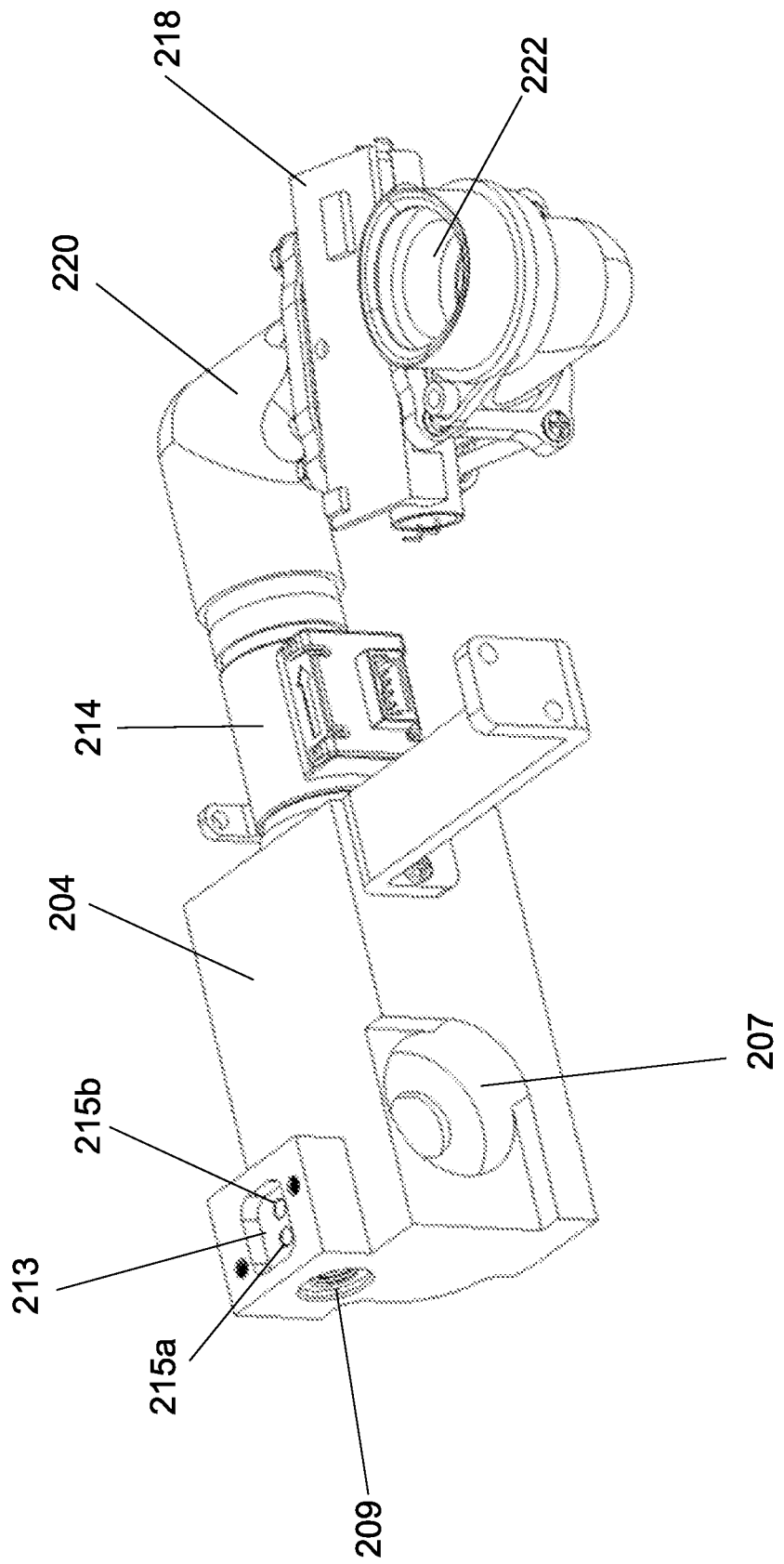
FIG. 3b shows the first port and second port of the mixing chamber.

With reference to FIG. 2, FIGS. 3a and 3b, the gas mixing mechanism 200 includes a first gas inlet 202 allowing entry of atmospheric air into a mixing chamber 204, a second gas inlet 206 connectable to a pressurized gas source for supplying a pressurized gas in particular, but not limited to, high pressure oxygen gas, to the mixing chamber 204. A sealing ring 208 may be provided between the second gas inlet 206 and the mixing chamber 204 to avoid or minimize leakage of the pressurized gas. The mixing chamber 204 also has a gas outlet 210 for discharging the mixed stream of gas, and a check valve 212. The check valve 212 may be provided at a recess 213 on the mixing chamber 204 to prevent back flow of the gas. The check valve 212 can be of any design an ordinary skill person in the art can appreciate. In this embodiment, the check valve 212 includes a silicone film arranged to cover the opening 215a. The silicone film or a part of the silicon film covering the opening 215a only allows an unidirectional gas flow from the second gas inlet 206 to the surrounding, and the opening 215b allows gas flows into the mixing chamber 204. For example, when the pressurized gas enters the respiratory apparatus 100 particularly into the mixing chamber 204, the pressure may be high enough to lift up the silicone film covering the opening 215a, and allows the pressurized gas to flow away via the opening 215a. The leaked gas may return to the mixing chamber 204 via the opening 215b, but not the opening 215a.

In this embodiment, the mixing chamber has a first port 207 for receiving the first gas inlet 202 and a second port 209 for receiving the second gas inlet 206. In this embodiment, the first gas port 207 is separate from, and aligned perpendicular to the second port 209. The first port may be connected to a blower 205 for receiving atmospheric air from the ambient environment. When the pressurized gas enters the respiratory apparatus 100 via the second gas inlet 206, the atmospheric air concurrently enters into the mixing chamber 204 via the first gas inlet 202 and mixes with the pressurized gas. The two streams of gas may then be thoroughly mixed in the mixing chamber 204. The resultant mixed stream of gas is then discharged past a flow sensor 214 downstream of and connected to the mixing chamber 204. In this embodiment, the flow sensor 214 is arranged to determine the flow rate of the mixed stream of gas after existing the mixing chamber 204 such that an operator can monitor the gas flow.

In this embodiment, a noise-damping member 216 is provided at one end; or the downstream end, of the flow sensor 214. In FIG. 2, the noise-damping member 216 is made of a sound absorbing material such as sintered porous PE that is capable of absorbing high frequency noises generated by the respiratory apparatus. In particular, the high frequency noises are typically those generated during the supply of the pressurized gas at the second gas inlet 206, and/or those generated during the mixing of the two steams of gas in the mixing chamber 204. The noise-damping member 216 is configured in cylindrical form with a size engagable with the flow sensor 214. The noise-damping damping member 216 engages with the flow sensor 214 at one end and allows the mixed stream of gas to continue to flow to another part of the respiratory apparatus 100. As shown in FIG. 2, the noise-damping member 216 has a cylindrical body 217a insertable into the flow sensor 214 and an end portion 217b with a diameter greater than the diameter of the cylindrical body 217a. The end portion 217b limits the movement of the noise-damping member 216 in the respiratory apparatus 100 so as to keep the noise-damping member 216 in place. The end portion 217b may also facilitate the connection between the flow sensor 214 and other components of the respiratory apparatus 100. Such a configuration of the noise-damping member 216 is useful in manufacturing process, and in minimizing noises with stable connection between the components.

In an embodiment, an additional noise-damping member 211 may be provided between the mixing chamber 204 and the flow sensor 214. The additional noise-damping member 211 may be provided as a porous membrane allowing gas to pass through. This can help to minimize turbulence in the mixed stream of gas before said gas enters the flow sensor 214. This arrangement can further help to reduce the noises. The additional noise-damping member 211 can be made of the sound absorbing material as described above.

In an embodiment where an ultrasonic sensor (see FIG. 3b at 218) is included in the respiratory apparatus 100 for detection of gas, the noise-damping member 216 is preferably positioned upstream of the ultrasonic sensor so as to absorb, reduce, or insulate most of, if not all, the undesirable high frequency noises for subsequent measurement performed downstream. This is particularly useful to improve the accuracy of detection conducted by the ultrasonic sensor.

As shown in FIG. 3a, an ultrasonic sensor 218 is arranged downstream of the flow sensor 214 and the noise-damping member 216 to determine the concentration of the pressurized gas in the mixed stream of gas, particularly oxygen content in the mixed gas passage 220. The mixed gas later enters into the humidifying chamber 102 via the tube 222. It is appreciated that in an embodiment where the respiratory apparatus does not include a flow sensor, the noise-damping member may be arranged anywhere along the flow path between the mixing chamber 204 and the humidifying chamber 102, and upstream of the ultrasonic sensor 218. It would also be appreciated that the noise-damping member 216 can be configured in any shape to be attached along the flow path.

Without intending to be limited by theory, it is believed that the presence of the noise-damping member 216 in the respiratory apparatus 100 of the present invention can improve the accuracy of gas detection and allow the operator to monitor the gas delivered to the user.

Furthermore, as shown in FIG. 1, the respiratory apparatus 100 may further include a noise reduction device 400 mounted on the housing 106, upstream of the mixing chamber, so as to further minimize noises created when supplying atmospheric air to the respiratory apparatus 100. FIG. 4 to FIG. 9 show an embodiment of the noise reduction device 400 which has a cover 402 and a body 404. The cover 402 and the body 404 are, preferably, separately manufactured and can be detachably engaged with each other through a locking means such as sliding or screwing.

In this embodiment, the cover 402 and the body 404 may be made of a plastic, such as a thermoset plastic, a resin, a polymeric material, etc. Such plastics are known in the art and typically include materials such as polycarbonate, polyethylene, polypropylene, polyvinyl chloride, acrylonitrile butadiene styrene, polymethyl methacrylate, phenolics, melamine formaldehyde, polysulfone, polyetherimide, polyethylene terephthalate, urea-formaldehyde, polyether ether ketone, and a combination thereof. Furthermore, the plastic may incorporate an anti-microbial compound by, for example, containing a coating, integrating the anti-microbial compound into the plastic, etc.

Figure 5:
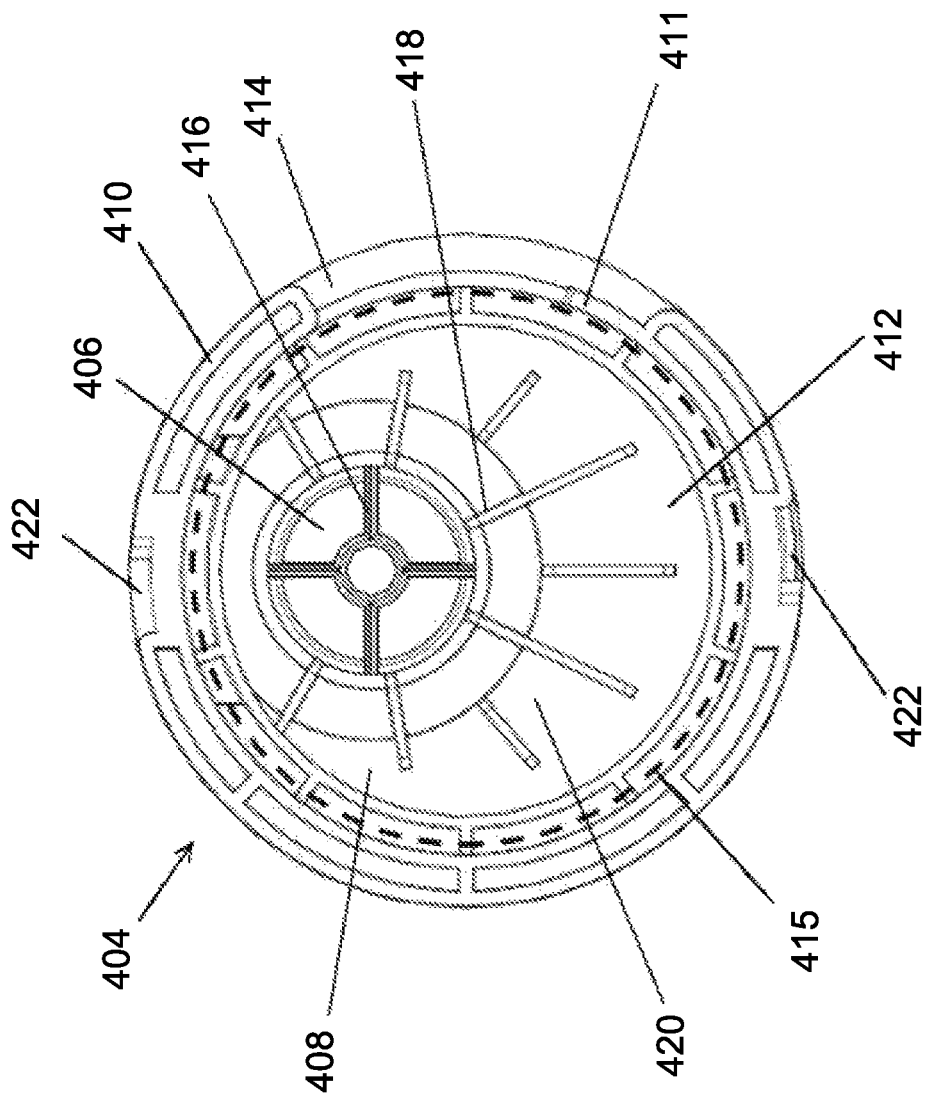
FIG. 5 shows a front view of an embodiment of the body before engaging with the cover.

FIG. 5 shows an embodiment of the body 404 before engaging with the cover 402. The body 404 has a noise reduction device gas outlet 406 and is mounted to the respiratory apparatus 100. In this embodiment, the body 404 is configured with a cavity 408 surrounded by a side wall 410. The side wall 410 extends perpendicularly from periphery of an inner surface 412 and includes a first end portion 411. The cavity 408 may be open or closed depending on the configuration of the side wall 410. In this embodiment, the cavity 408 is open with the side wall 410 configured as a C-shape, i.e. leaving an open portion 414. At least part of the side wall 410 can be coupled to the cover 402 for forming a tight seal.

The cavity 408 may house a filter 415 (shown as a dotted line) therein. The filter 415 may be provided to filter dust, pollen, mold, bacteria, etc. from the gas, particularly atmospheric air, before the gas enters the respiratory apparatus. In an embodiment where the filter 415 is detachably arranged in the cavity 408 of the body 404, the filter 415 can be replaced with a new one either randomly or regularly so as to keep the filtered gas free from, or at least with a reduced amount of, dust, pollen, mold, bacteria, etc. Without intending to be limited by theory, it is believed that this is particularly advantageous when the respiratory apparatus is used for clinical applications. It is also believed that the filter 415 can also act as a noise suppressor to reduce the noise generated in the cavity 408 when the gas passes through the noise reduction device 100. The filter 415 may be, for example, a paper filter, a foam filter, a cotton filter, a high-efficiency particulate air filter, a HEPA filter, etc. as desired. One skilled in the art would appreciate that various suitable filters can be applied to the noise reduction device 100 of the present invention.

In this embodiment, the noise reduction device gas outlet 406 is radially offset and is supported by a supporting structure 416 which has a plurality of upright protrusions 418 on the inner surface 412 connecting to the noise reduction device gas outlet 406. The noise reduction device gas outlet 406 may be aligned with the gas pathway in the respiratory apparatus, thereby reducing the formation of turbulence. One skilled in the art would appreciate that the noise reduction device gas outlet 406 may be positioned at the centre of the cavity 408 to achieve the similar purpose.

The cavity 408 may further include a converging portion 420 on the inner surface 412 which converges towards the noise reduction device gas outlet 406 so as to facilitate the gas flow. In addition to guiding the flow of the gas towards the noise reduction device gas outlet 406, the supporting structure 416 may also help to hold the filter 415 in place. Without intending to be limited by theory, it is also believed that the upright protrusions 418 and supporting structure 416 may further enhance the structural integrity of the body 404 and/or the cover 402. The upright protrusions 418 and the converging portion 420 support the filter 415 which may help to separate the filter 415 from the inner surface 412 to increase the effective surface area of the filter 415 and hence increase the amount of filtered gas flow. This may synergistically help to protect a blower 205 of the respiratory apparatus 100 by reducing its workload and thus further reducing the noise produced. In this embodiment, the upright protrusions 418 of the supporting structure 416 are configured as extending, continuously or discontinuously, radially from the noise reduction device gas outlet 406.

Figure 4:
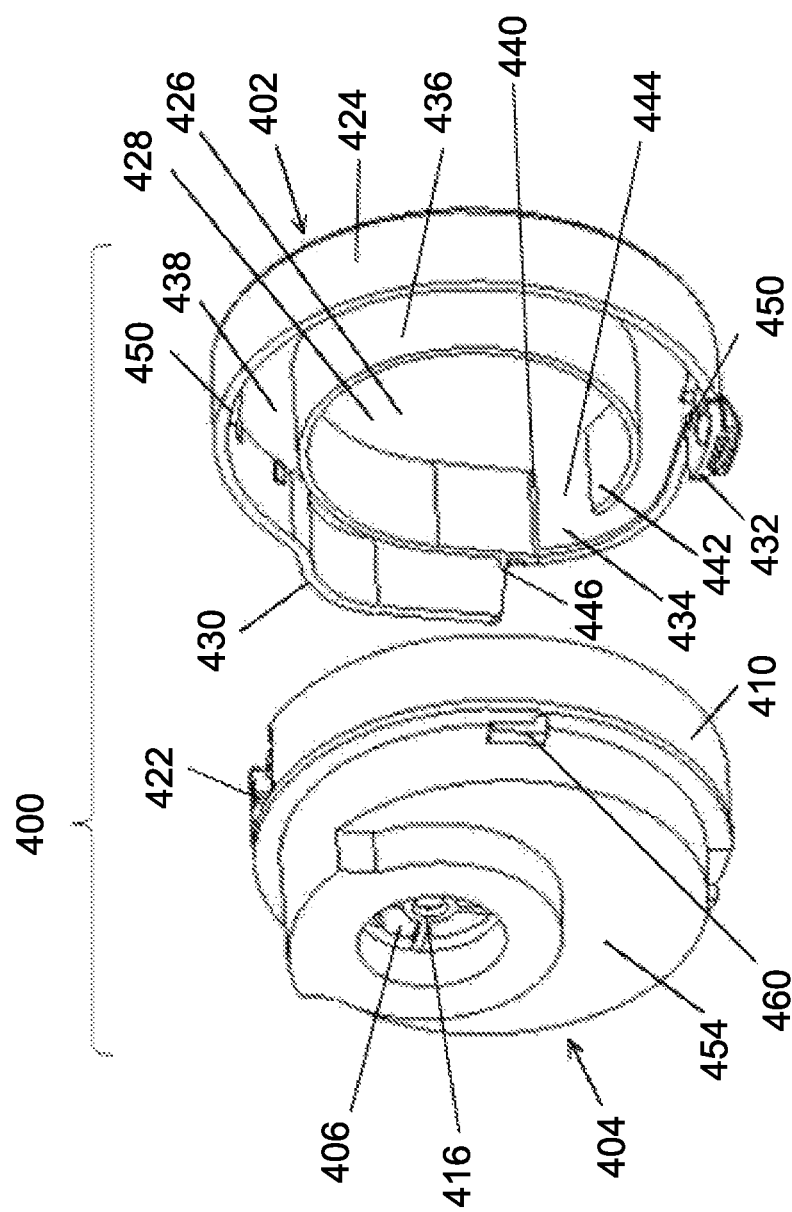
FIG. 4 shows a perspective view of an embodiment of the noise reduction device, which may be included in the respiratory apparatus, with the body and the cover of the noise reduction device being disengaged from each other.

In the embodiment of FIGS. 4 and 5, the body 404 is configured to detachably engage with the cover 402. Preferably, the body 404 is enclosed by the cover 402 after engaging with the cover 402. The body 404 may include two slots 422 (or tabs) respectively arranged on substantially diametrically opposite sides of the side wall 410 for complementary slide locking with corresponding tabs (or slots) on the cover 402.

Figure 6:
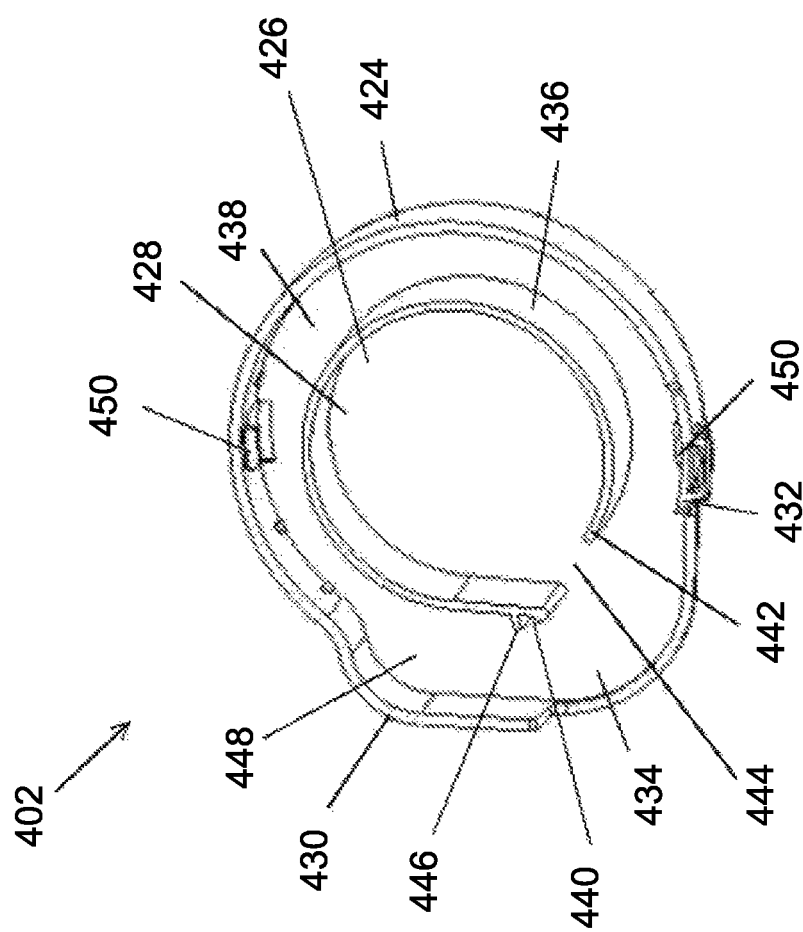
FIG. 6 shows a rear view of the embodiment of the cover of FIG. 4.

Turning to the cover 402, with reference to FIG. 6 showing a rear view of it, the cover 402 has a side wall 424 and an inner surface 426 facing towards the inner surface (see FIG. 5 at 412) of the body 404 when it is engaged with the body 404 to form the noise reduction device 100. The side wall 424 extends perpendicularly from the periphery of the inner surface 426 and partially surrounds the cover 402 to form a cavity 428. In this embodiment, the cavity 428 is open with the side wall 424 configured substantially as a C-shape to define a second end portion 430 and a third end portion 432 on the side wall 424 respectively, leaving an open portion 434.

The cover 402 has a guiding member 436 being configured to extend substantially perpendicularly from the inner surface 426. The guiding member 436 itself defines at least a part of a gas passage 438, and is configured in a way to form the gas passage 438 between the body 404 and the cover 402 when they are engaged together. One skilled in the art would appreciate that possible configurations of the guiding member such as a spiral including Cotes's spiral, Archimedean spiral and golden spiral, may be used depending on the desired design and noise reduction requirements. Preferably, the area enclosed by the guiding member 436 is at least twice than area of the noise reduction device gas outlet 406 in order to increase the effective filtering area of the filter 415 and reduce gas resistance, thereby further reducing noise production.

In this embodiment, the guiding member 436 is substantially in form of a C-shape. The guiding member 436 has a fourth end portion 440 and a fifth end portion 442 defining an opening 444 aligning with the open portion 434 and to be closed by the side wall 410 of the body 404 when the body 404 and the cover 402 are engaged. The fourth end portion 440 includes a projection 446 for additional engagement and position fixing with the first end portion 411 of the body 404 when the body 404 and the cover 402 are engaged together.

The fourth end portion 440 and the second end portion 430 together define a flow deflecting portion 448 being a part of the gas passage 438 to provide an enlarged section for an increased level of gas entry, and facilitate a spiral flow of the gas into the gas passage. The flow deflecting portion 448 may also avoid transmission of noise from the blower inside the respiratory apparatus to the outside environment.

In this embodiment, the cover 402 is detachably engageable with the body 404 and preferably encloses the body 404 after engagement. Similar to the body 404, two tabs 450 may be respectively arranged on substantially diametrically opposite sides of the side wall 424 for complementary slide locking with corresponding slots 422 on the body 404 to form a bayonet mount.

Figure 7:
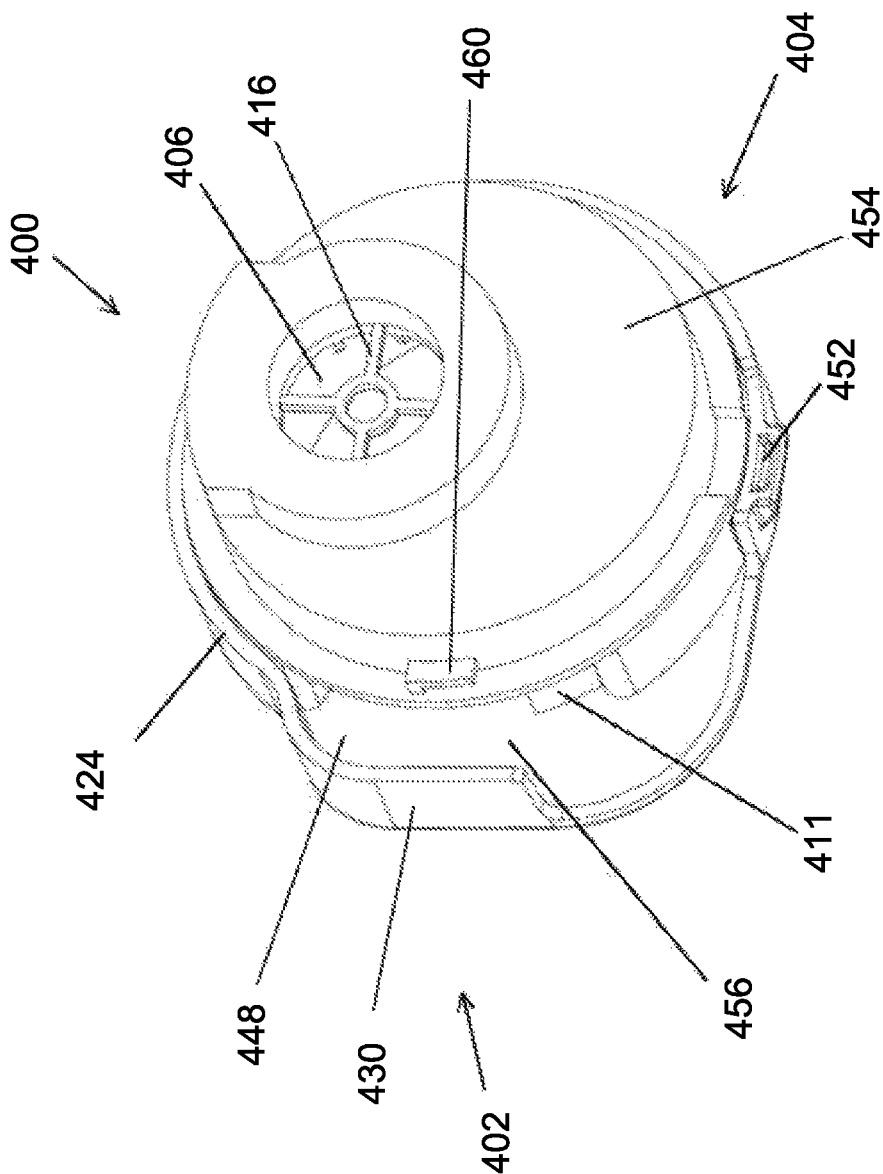
FIG. 7 shows an embodiment of the noise reduction device when the body and the cover are engaged.

FIG. 7 shows the noise reduction device 400 when the body 404 and the cover 402 are slidably locked to one another. In this embodiment, the body 404 is oriented and inserted into the cavity (see FIG. 6 at 428) of the cover 402 with the tabs (see FIG. 6 at 450) being received in the slots (see FIG. 5 at 422). A slight turning of either the body 404 or the cover 402 locks the two components with a bayonet lock as a locking mechanism 452 to hold them in place. In the present invention, the locking mechanism 452 includes at least one slot 422 arranged on the body 404, and at least one corresponding tab (see FIG. 6 at 450) arranged on the cover 402. In another embodiment, the locking mechanism 452 may include a pair of magnetic members arranged on the cover 402 and the body 404 as the locking means. One skilled in the art would appreciate that other locking means, such as a push lock, a slide lock, a screw, a plug and/or a combination thereof, may be used herein.

In this figure, the outer surface 454 of the body 404 shows the noise reduction device gas outlet 406 which is to be mounted to the respiratory apparatus 100 for fluid communication with the blower 205 inside the respiratory apparatus 100. The flow deflecting portion 448, which is not covered by the body 404, is shown adjacent to the second end portion 430 of the side wall 424. Adjacent to the flow deflecting portion 448 is a noise reduction device gas inlet 456 arranged between the side wall (see FIG. 5 at 410) and the side wall 424. The first end portion 411 of the side wall 410 is arranged adjacent to the noise reduction device gas inlet 456. Two tabs 460 (only one is shown) are disposed on substantially diametrically opposite ends of the outer surface 454 for detachable mounting on the respiratory apparatus 100 through sliding. One skilled in the art would appreciate that other locking means such as screwing may also be used depending on the configuration of the respiratory apparatus.

Figure 8:
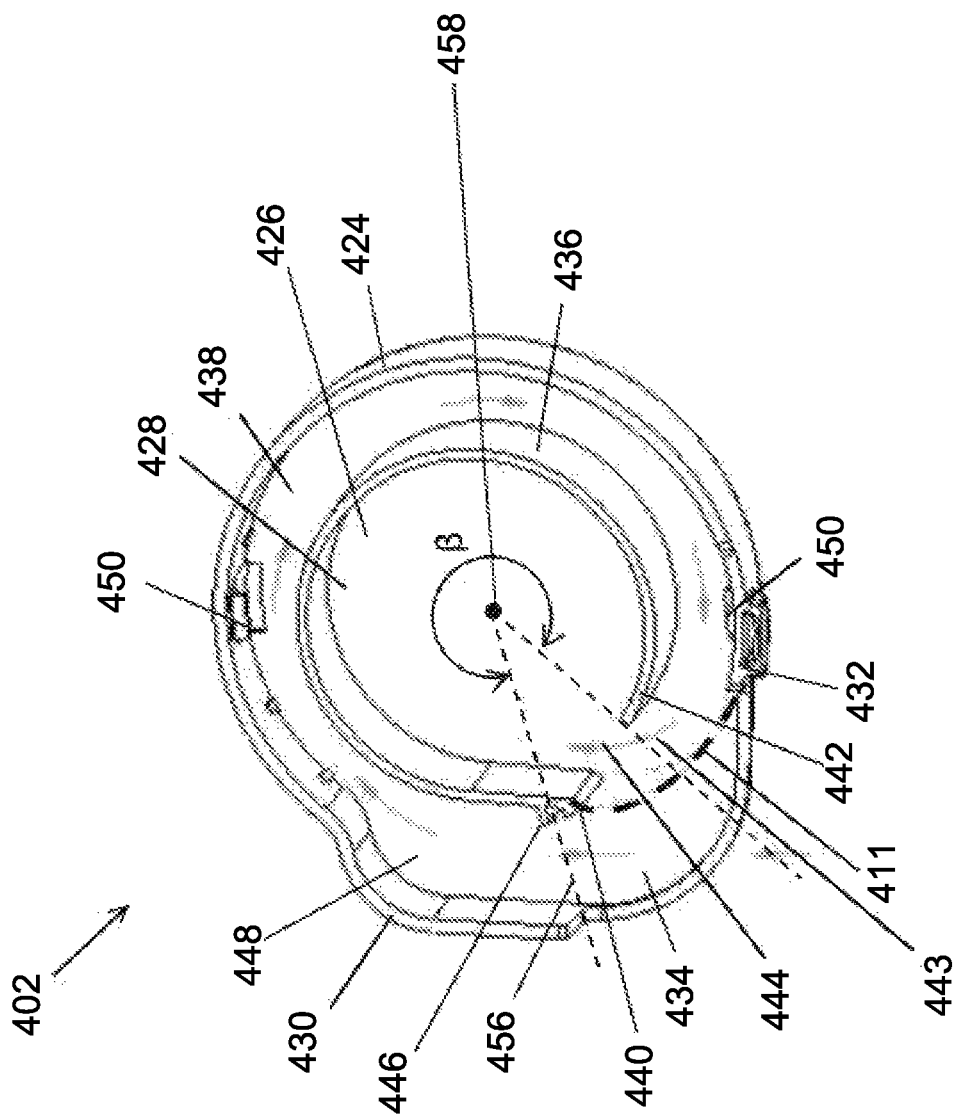
FIG. 8 shows the direction of the gas flow in an embodiment of the noise reduction device when the body is engaged with the cover.

Referring to FIG. 8, when the body 404 and the cover 402 are engaged, the side wall 410 of the body 404 is received in the gas passage 438 and the body 404 is enclosed by the cover 402. The location of the first end portion 411 is shown as a dotted line forming a seal with the projection 446 and abutting the fourth end portion 440 of the guiding member 436 to define the planar spiral gas passage 438 between the side wall 410 and the guiding member 436, wherein the fifth end portion 442 spaces apart from the side wall 410 to form a gap 443 and the noise reduction device gas inlet 456 is arranged to be perpendicularly to the noise reduction device gas outlet 406 in this embodiment. In an embodiment where a filter (see FIG. 5 at 415) is placed in the body 404, the guiding member 436 is in contact with the filter 415 when the body 404 and the cover 402 are engaged so as to keep the filter 415 in place by sandwiching the filter 415 between the guiding member 436 and the body 404. This also helps to avoid oscillation of the filter 415 between the body 404 and the cover 402 when the gas passes the filter 415.

During operation, the atmospheric air is drawn to the noise reduction device gas inlet 456 preferably by the blower 205 of the respiratory apparatus 100, where the gas travels from the flow deflecting portion 448 of a wider cross section to the gas passage 438 of a narrower cross section for a smoother gas flow by maintaining or even reducing gas resistance. The gas then flows through the gas passage 438, the gap 443, and to the opening 444. The gas then passes through the filter 415 which is in contact with the guiding member 436 when the body 404 and the cover 402 are engaged, and finally reaches the noise reduction device gas outlet 406 (shown by arrows). One skilled in the art would appreciate that with such configuration, the incoming gas is forced to travel an angular rotation β about a centre 458 of the noise reduction device gas outlet 406 of at least 330 degrees from the noise reduction device gas inlet 456 to the noise reduction device gas outlet 406. In an alternative embodiment, the gas passage 438 formed may direct the gas flow to travel an angular rotation β about the centre 458 of the noise reduction device gas outlet 406 of at least 180 degrees, at least 270 degrees or at least 300 degrees, relative to the noise reduction device gas inlet 456 before discharging at the noise reduction device gas outlet 406.

Figure 9:
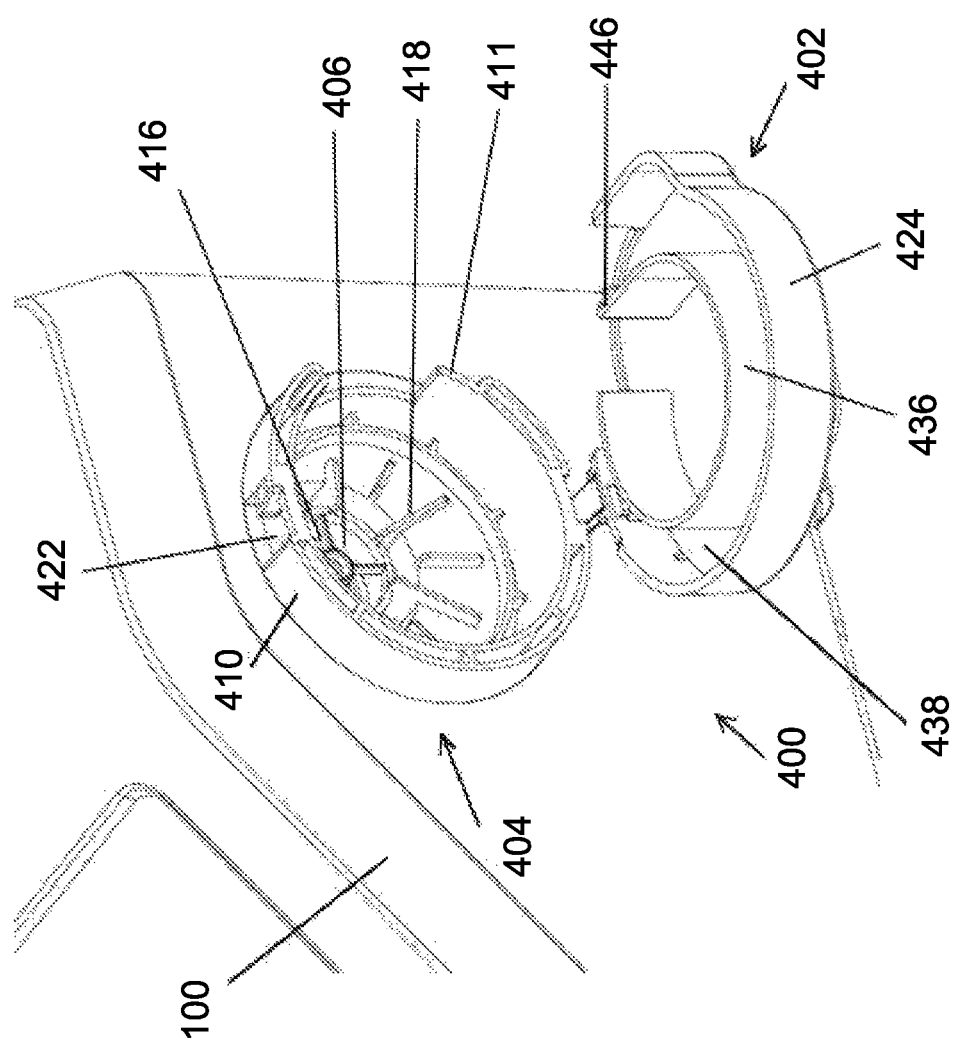
FIG. 9 shows an embodiment of the noise reduction device being mounted to the respiratory apparatus herein; and The figures herein are for illustrative purposes only and are not necessarily drawn to scale.

With reference to FIG. 9, the noise reduction device 400 is mounted to the respiratory apparatus 100. The body 404 is mounted to one side of the respiratory apparatus 100 by the tabs 460. The tabs 450 on the cover 402 are oriented to be slidably locked with the corresponding slots 422. A seal is to be formed by the first end portion 411 and the projection 446 of the guiding member 136 to define the gas passage 438.

The noise reduction device 400 in the present invention can provide obvious noise reduction effect at the first gas inlet by decreasing the turbulence and resistance of gas flow to a larger extent and thus reducing the noise caused by the friction between the fluctuated gas flow and the noise reduction device gas inlet particularly before mixing the atmospheric air with the pressurized gas. Moreover, the configuration of the guiding member 436 being located on the cover 402 provides an easier and more convenient way to clean the gas passage 438. The cover 402 can be disengaged from the body 404 and subject to common sterilization methods of medical equipment. Such arrangement also facilitates replacement of the cover 402 in case abrasion or damage is found on the guiding member 436 which may increase turbulent flow of the incoming gas and thus causes noise.

According to the above, it is believed that the respiratory apparatus of the present invention and that coupled with the noise reduction device as described above can generate less noise during operation and allow better measurement of gas content. The respiratory apparatus herein poses substantial improvements over the existing apparatus.

It should be understood that the above only illustrates and describes examples whereby the present invention may be carried out, and that modifications and/or alterations may be made thereto without departing away from of the invention.

It should also be understood that certain features of the invention, which are, for clarity, described in the context of separate embodiments, may also be provided in combination in a single embodiment. Conversely, various features of the invention which are, for brevity, described in the context of a single embodiment, may also be provided separately, or in any suitable subcombination.

The invention claimed is:

1. A respiratory apparatus, comprising:
a first gas inlet for supplying a first gas to the respiratory apparatus;
a second gas inlet connectable to a pressurized gas source to supply a pressurized gas;
a mixing chamber for mixing the first gas and the pressurized gas; and
a noise-damping member disposed downstream of the mixing chamber;
wherein the mixing chamber comprises a gas outlet for discharging a mixed stream of gas towards a humidifying chamber;
wherein the respiratory apparatus further comprises a flow sensor for determining a flow rate of the mixed stream of gas towards the humidifying chamber; and
wherein the noise-damping member is cylindrical, and has a cylindrical body insertable into the flow sensor and an end portion with a diameter greater than the diameter of the cylindrical body.

2. The respiratory apparatus of claim 1, further comprising a sensor for determining concentration of one or more gas components in a gas selected from a group consisting of the first gas, the pressurized gas, and the mixed stream of gas.

3. The respiratory apparatus of claim 2, wherein the sensor is an ultrasonic sensor disposed downstream of the noise-damping member.

4. The respiratory apparatus of claim 1, wherein the noise-damping member is in fluid communication with the mixing chamber.

5. The respiratory apparatus of claim 1, wherein the noise-damping member comprises a sound absorbing material.

6. The respiratory apparatus of claim 1, wherein the noise-damping member is made of a sintered material.

7. The respiratory apparatus of claim 1, wherein the noise-damping member comprises a sintered porous plastic selected from sintered porous polyethylene, sintered porous polyamide, sintered porous polytetrafluoroethylene, or sintered porous polyvinylidene fluoride.

8. The respiratory apparatus of claim 1, wherein the mixing chamber receives the first gas at a first port and the pressurized gas at a second port.

9. The respiratory apparatus of claim 8, wherein the first port is aligned perpendicular to the second port.

10. The respiratory apparatus of claim 1, wherein the first gas inlet supplies atmospheric air and wherein the pressurized gas is oxygen; or high pressure oxygen.

11. The respiratory apparatus of claim 1 further comprises a noise reduction device mounted on the respiratory apparatus.

12. The respiratory apparatus of claim 11, wherein the noise reduction device comprises a body having a side wall and a noise reduction device gas outlet; and a cover configured to be detachably engageable with the body for forming a noise-reduction device gas inlet and a gas passage.

13. The respiratory apparatus of claim 12, wherein the cover of the noise reduction device comprises a guiding member defining at least a part of the gas passage, wherein the guiding member is configured to be coupled with the side wall of the body to form the gas passage between the body and the cover.

14. The respiratory apparatus of claim 12, wherein the gas passage formed directs a flow of gas to an angular rotation about a centre of the gas outlet of at least 180 degrees to 330 degrees relative to the gas inlet before discharging at the gas outlet.

15. The respiratory apparatus of claim 13, wherein the guiding member is in the form of a C-shape.

16. The respiratory apparatus of claim 13, wherein the guiding member comprises an end portion forming a seal with a side wall of the body.

17. The respiratory apparatus of claim 11, wherein the noise reduction device is in fluid communication with the first gas inlet.

18. The respiratory apparatus of claim 11, wherein the noise reduction device is upstream of the mixing chamber.

* * * * *